United States Patent [19]

Iwama et al.

[11] Patent Number: 5,076,277
[45] Date of Patent: Dec. 31, 1991

[54] CALCULUS DESTROYING APPARATUS USING FEEDBACK FROM A LOW PRESSURE ECHO FOR POSITIONING

[75] Inventors: Nobuyuki Iwama; Satoshi Aida, both of Tokyo, Japan

[73] Assignee: Kabushiki Kaisha Toshiba, Kawasaki, Japan

[21] Appl. No.: 704,845

[22] Filed: May 20, 1991

Related U.S. Application Data

[63] Continuation of Ser. No. 480,008, Feb. 14, 1990, abandoned.

[30] Foreign Application Priority Data

Feb. 17, 1989 [JP] Japan .................................. 1-37638

[51] Int. Cl.$^5$ .............................................. A61B 17/22
[52] U.S. Cl. ............................ 128/660.03; 128/24 EL
[58] Field of Search ............... 128/660.03, 24 EL, 804

[56] References Cited

U.S. PATENT DOCUMENTS

| | | | |
|---|---|---|---|
| 4,537,074 | 8/1985 | Dietz . | |
| 4,771,787 | 12/1986 | Wurster et al. . | |
| 4,803,995 | 6/1987 | Ishida et al. . | |
| 4,858,597 | 8/1989 | Kurtze et al. | 128/24 EL |
| 4,888,746 | 12/1989 | Wurster et al. | 128/24 EL |

FOREIGN PATENT DOCUMENTS

| | | |
|---|---|---|
| 0102179 | 3/1984 | European Pat. Off. . |
| 0225104 | 6/1987 | European Pat. Off. . |
| 3119295 | 12/1982 | Fed. Rep. of Germany . |
| 60-145131 | 7/1985 | Japan . |

*Primary Examiner*—Ruth S. Smith
*Attorney, Agent, or Firm*—Oblon, Spivak, McClelland, Maier & Neustadt

[57] ABSTRACT

A calculus destroying apparatus includes piezoelectric elements constituted by arranging a plurality of piezoelectric elements to have a predetermined shape, thereby constituting a shock wave generating source, a first driver for driving the piezoelectric elements by a high voltage pulse so that a shock wave for calculus destruction having a predetermined focal point pressure distribution is generated from the piezoelectric elements, a second driver for driving at least some of the piezolectric elements by a low voltage pulse so that a low pressure ultrasonic wave having a lower pressure and a wider focal point pressure distribution than those of the shock wave is generalized from the piezoelectric elements, a receiver for receiving an echo of the low pressure ultrsonic wave from inside a patient's body via the piezoelectric elements, and a controller for activating the second driver prior to activation of the first driver, and activating the first driver when the intensity of the echo received by the receiver exceeds a predetermined threshold value.

16 Claims, 5 Drawing Sheets

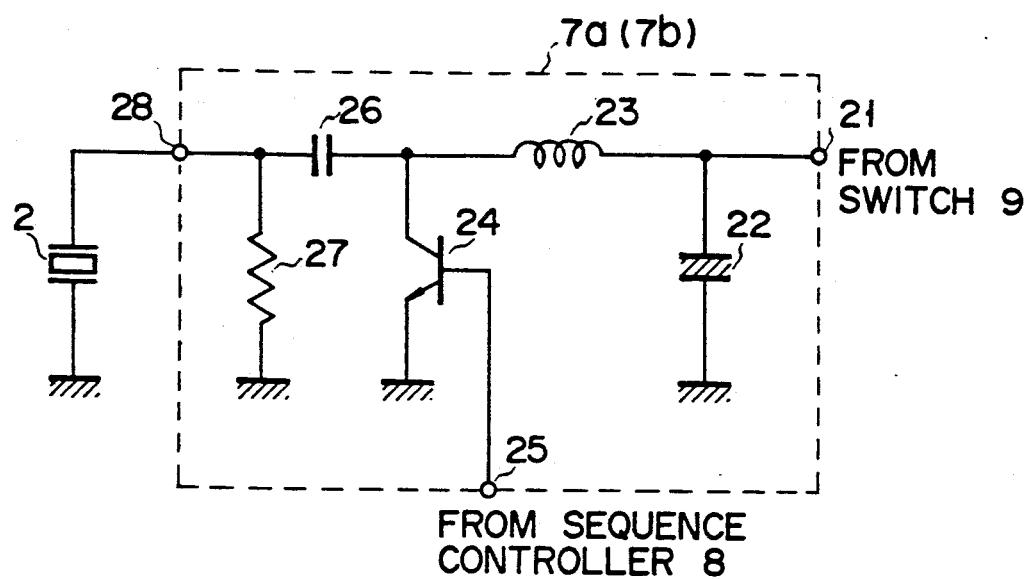
FIG. 3
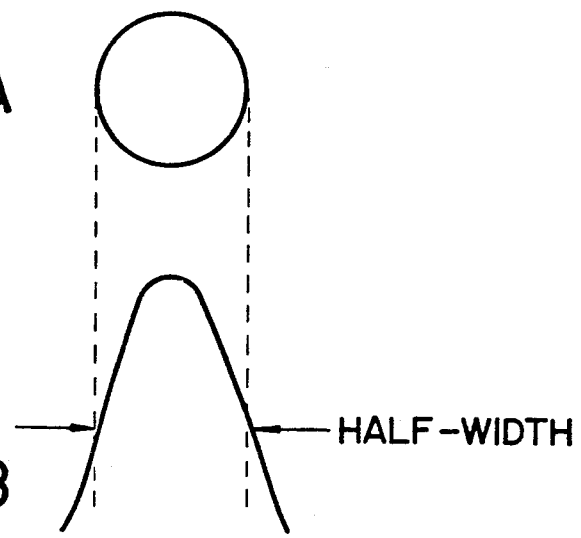
FIG. 5A
FIG. 5B

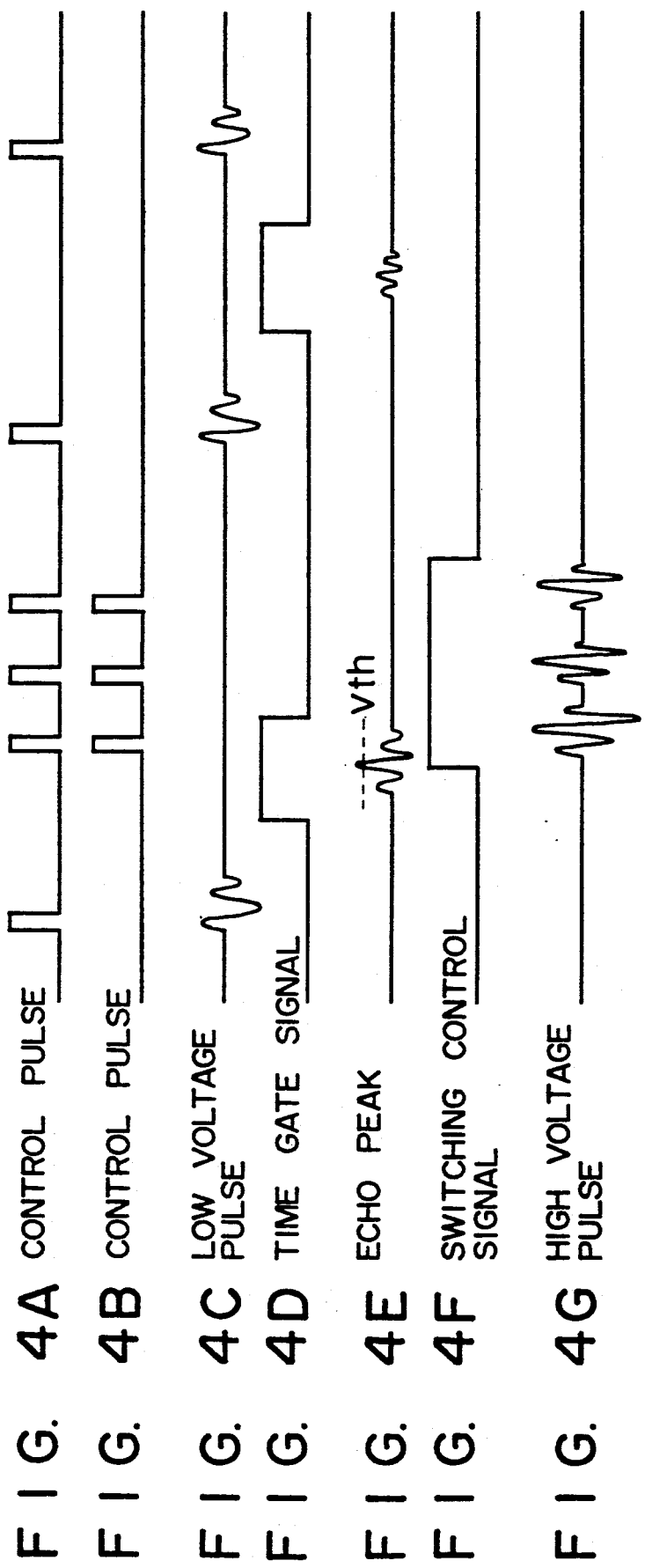

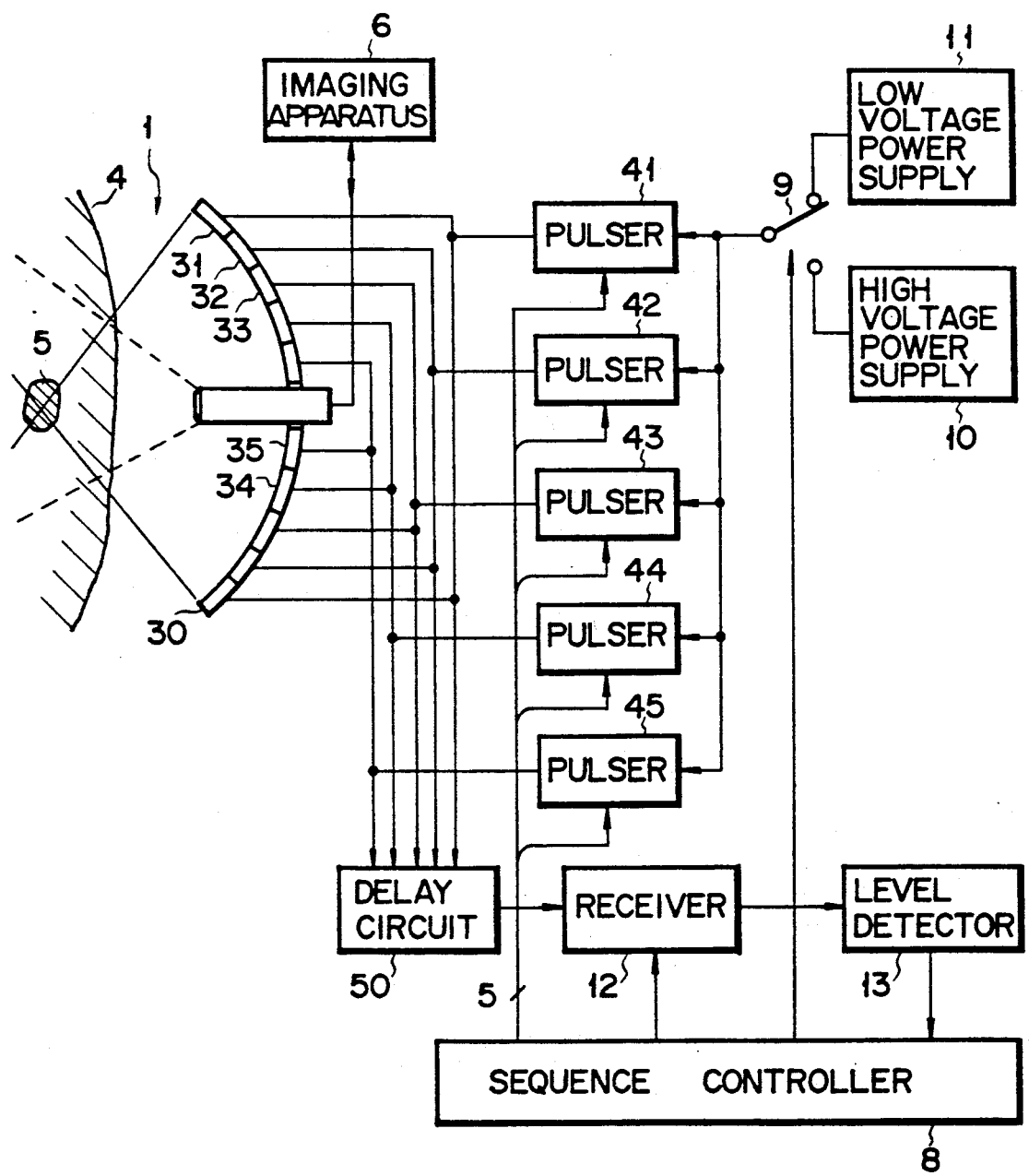
F I G. 6

CALCULUS DESTROYING APPARATUS USING FEEDBACK FROM A LOW PRESSURE ECHO FOR POSITIONING

This application is a continuation of application Ser. No. 07/480,008, filed on Feb. 14, 1990, now abandoned.

BACKGROUND OF THE INVENTION

1. Field of the Invention

The present invention relates to a calculus destroying apparatus for destroying a calculus by using a shock wave and, more particularly, to a calculus destroying apparatus using piezoelectric elements as a shock wave source.

2. Description of the Related Art

Recently, as a method of removing a calculus such as a renal calculus without performing an operation, a method of destroying a calculus by focusing a shock wave onto a calculus portion in a body from an external shock wave source has been proposed and widely used. This method less invades a patient, i.e., a living body than an operation. If, however, a focal point of a shock wave falls outside a calculus portion and the focused shook wave is radiated onto a normal tissue, a side effect on the normal tissue cannot be prevented. Actually, a calculus portion often falls outside a focal point of a shock wave source due to a respiratory motion or a body motion of a patient.

A calculus destroying apparatus which copes with the above problem is disclosed in U.S. Pat. No. 4,803,995. This calculus destroying apparatus employs piezoelectric elements as a shock wave source and operates such that a low pressure ultrasonic wave in the same focused state as a shock wave is radiated in a body via the piezoelectric elements for calculus destruction and the coincidence between a focal point of the shock wave source and a calculus portion is determined in accordance with the intensity of an echo from a portion near the focal point. According to this apparatus, since a shock wave is radiated only when a focal point and a calculus portion coincide with each other, erroneous radiation caused by, e.g., a respiratory motion can be prevented.

Generally, piezoelectric elements used to generate a shock wave for calculus destruction are accurately concavely arranged to form a pressure distribution extremely focused to have a half amplitude width, i.e., half width, in the radial direction of about 2 to 4 mm so that a very high pressure of about 600 kbar to 1 kbar is obtained at a focal point. A low pressure ultrasonic wave focused to the same degree as this calculus destroying shock wave was radiated on a spherical target shown in FIG. 1A as a model calculus, and a peak value distribution of its echo intensity was measured. The measurement result is shown in FIG. 1B. An active alumina sphere having a diameter of 7 mm was used as the spherical target. Referring to FIG. 1B, peak values of the echo intensity obtained when the spherical target was moved in the direction of depth of the focal point and perpendicularly to a central axis are plotted. In this case, the half width of the echo intensity distribution shown in FIG. 1B becomes 4 mm which is 57% of the diameter of the target.

Assume that in the above conventional technique, when the echo intensity reaches the intensity of the half value, i.e., ½ or more the maximum intensity, it is determined that a focal point of a shock wave source coincides with a calculus portion, and a shock wave is radiated. In this case, it is expected that the shock wave can be radiated on a portion only about 57% the diameter of a calculus but cannot be radiated on its end portion.

SUMMARY OF THE INVENTION

As described above, in the conventional technique, a coincidence between a calculus portion and a focal point of a shock wave source is detected by using an ultrasonic wave having a lower pressure than that of a shock wave, and radiation of a shock wave is simply controlled on the basis of the detection result. Therefore, if the focal point is located at an end portion of a calculus, the echo intensity is reduced to disable detection of the coincidence between the calculus portion and the focal point of the shock wave source, and no shock wave is radiated accordingly. As a result, the shock wave cannot be radiated on the entire calculus.

It is, therefore, an object of the present invention to provide a calculus destroying apparatus capable of effectively radiating a shock wave on the entire calculus without radiating the shock wave on a portion except for the calculus.

A calculus destroying apparatus of the present invention comprises low pressure ultrasonic wave generating means for generating a low pressure ultrasonic wave having a lower pressure and a wider focal point pressure distribution than those of a shock wave for calculus destruction. In this apparatus, an echo of the low pressure ultrasonic wave from inside a patient's body is received, and shock wave generating means is activated when the intensity of the echo exceeds a predetermined threshold value.

More specifically, a calculus destroying apparatus of the present invention comprises piezoelectric elements constituted by arranging a plurality of piezoelectric elements to have a predetermined shape, thereby constituting a shock wave generating source, a first driver for driving the piezoelectric elements by a high voltage pulse so that a shock wave for calculus destruction having a predetermined focal point pressure distribution is generated from the piezoelectric elements, a second driver for driving at least some of the piezoelectric elements by a low voltage pulse so that a low pressure ultrasonic wave having a lower pressure and a wider focal point pressure distribution than those of the shock wave is generated from the piezoelectric elements, a receiver for receiving an echo of the low pressure ultrasonic wave from inside a patient's body via the piezoelectric elements, and a controller for activating the second driver prior to activation of the first driver, and activating the first driver when an intensity of the echo received by the receiver exceeds a predetermined threshold value.

The above piezoelectric elements are constituted by concentrically arranging a plurality of piezoelectric elements, and the low pressure ultrasonic wave having a wide focal point pressure distribution is generated by driving piezoelectric elements at only an inner peripheral portion, i.e., a portion near the center by the second driver, or by driving each piezoelectric element of the piezoelectric elements with a predetermined time difference.

When a coincidence between a calculus portion and a focal point is determined by using a low pressure ultrasonic having a wider focal point pressure distribution than that of a shock wave for calculus destruction, the echo intensity exceeds a threshold value and the shock wave is generated even if the focal point coincides with an end portion of the calculus. As a result, the shock wave can be radiated on substantially the entire calculus.

According to the calculus destroying apparatus of the present invention, a coincidence between a focal point of a shock wave source and a calculus portion is determined by using a low pressure ultrasonic wave having a wider focal point pressure distribution than that of a shock wave. Therefore, the shock wave can be accurately radiated on the entire calculus without erroneously radiating the shock wave on a normal tissue around the calculus. As a result, a side effect can be reduced and a calculus destroying effect can be improved.

BRIEF DESCRIPTION OF THE DRAWINGS

FIG. 3 is a circuit diagram showing in detail an arrangement of a pulser of the apparatus shown in FIG. 2;

FIGS. 4A to 4G are timing charts for explaining an operation of the apparatus shown in FIG. 2;

FIGS. 5A and 5B are views for explaining effects of the apparatus shown in FIG. 2 and show a spherical target and a peak value distribution of the echo intensity from the target;

FIG. 6 is a block diagram showing an arrangement of a calculus destroying apparatus according to the second embodiment of the present invention;

DETAILED DESCRIPTION OF THE PREFERRED EMBODIMENTS

Embodiments of the present invention will be described in detail below with reference to the accompanying drawings.

Figure 1A:
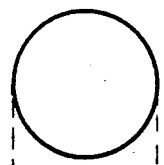
FIGS. 1A and 1B are views for explaining problems of the conventional technique and show a spherical target as a model calculus and a peak value distribution of the echo intensity from the target.
Figure 1B:
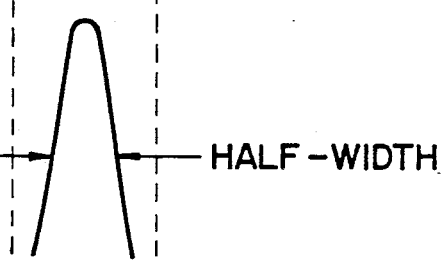
Figure 2:
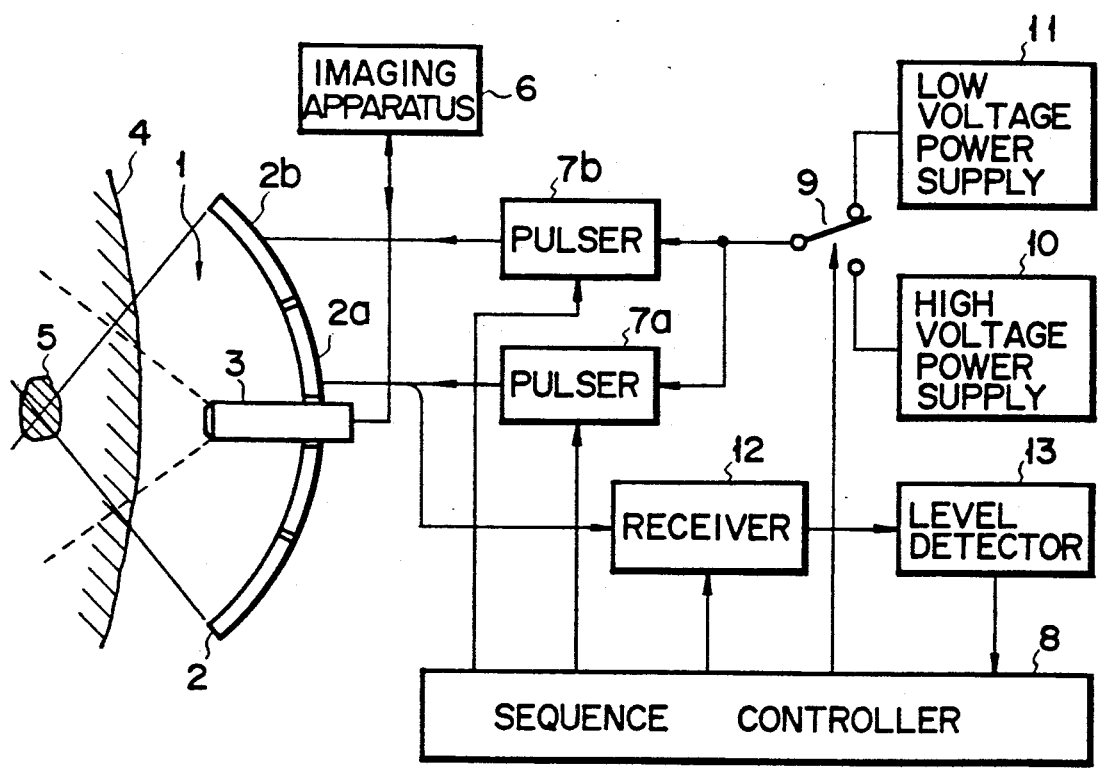
FIG. 2 is a block diagram showing an arrangement of a calculus destroying apparatus according to the first embodiment of the present invention.

FIG. 2 shows an arrangement of a calculus destroying apparatus according to the first embodiment of the present invention.

A treatment applicator 1 includes piezoelectric elements 2 constituted by concentrically arranging a plurality of ring-like piezoelectric elements and arranged spherically as a whole to form a concave ultrasonic transmitting/receiving surface, and an imaging ultrasonic probe 3 inserted at the center of the piezoelectric elements 2. In order to increase a transmission efficiency of an ultrasonic wave (including a shock wave) from the piezoelectric elements 2 to a patient 4 to enable efficient destruction of a calculus 5 in the body of the patient 4, a water bag (not shown), for example, is provided at an ultrasonic transmitting/receiving surface portion of the applicator 1. The water bag consists of a flexible material and contains an ultrasonic medium solution, e.g., water.

The imaging ultrasonic probe 3 is arranged to be movable in the axial direction (direction along its axis) and the rotational direction (rotational direction about the axis). An imaging device 6 transmits an ultrasonic wave into the body of the patient 4 via the probe 3 and receives an echo, thereby displaying an ultrasonic B mode image on a display (not shown). An operator (e.g., a doctor) moves the applicator 1 so that the focal point of the piezoelectric elements 2 coincides with the calculus 5 while observing the B mode image.

In this embodiment, the piezoelectric elements 2 are divided into an inner peripheral portion 2a and an outer peripheral portion 2b which can be driven independently of each other and are connected to pulsers 7a and 7b as pulse generating portions, respectively. The pulsers 7a and 7b are driven under the control of a sequence controller 8. A high voltage power supply 10 and a low voltage power supply 11 are selectively connected to a power input terminal of each of the pulsers 7a and 7b via a switch 9 controlled by the sequence controller 8.

The inner peripheral portion 2a of the piezoelectric elements 2 is connected to a receiver 12. Of echoes from the body of the patient 4 received by the inner peripheral portion 2a of the piezoelectric elements 2, the receiver 12 extracts only a signal from a portion close to the focal point in accordance with a time gate signal from the sequence controller 8, and amplifies and detects the extracted signal. An output signal from the receiver 12 is supplied to a level detector 13 and its level, i.e., echo intensity is detected. An output signal from the level detector 13 is supplied to the sequence controller 8.

FIG. 3 shows in detail an arrangement of one of the pulsers 7a and 7b. Referring to FIG. 3, a power input terminal 21 is connected to one end of a charge storing capacitor 22 and is also connected to the collector of a switching transistor 24 and one end of a coupling capacitor 26 via an inductor 23. The other end of the coupling capacitor 26 is connected to one end of a damping resistor 27 and an output terminal 28. The other end of the capacitor 22, the emitter of the transistor 24, and the other end of the damping resistor 27 are grounded. The base of the transistor 24 is connected to the sequence controller 8 shown in FIG. 2 via a control input terminal 25.

A control pulse is supplied from the sequence controller 8 to the base of the transistor 24 via the control input terminal 25. When the transistor 24 is turned on, a charge stored in the capacitor 22 is discharged via the inductor 23 and the transistor 24, and the potential of the output terminal 28 abruptly varies in the negative direction (drops) accordingly. When the transistor 24 is turned off, a counterelectromotive force of the inductor 23 is generated to raise the potential of the output terminal 28 in the positive direction. In this case, an inductance value of the inductor 23 is adjusted to be tuned to a resonance frequency of the piezoelectric elements, and the pulse width of the control pulse supplied to the control input terminal 25 is set to be a ½ value the resonance frequency. As a result, a pulse voltage about twice (p - p value) the voltage of the high or low voltage power supply 10 or 11 appears at the output terminal 28.

An operation of the apparatus having the above arrangement will be described below with reference to timing charts shown in FIG. 4A-4G.

The switch 9 normally connects the low voltage power supply 11 to the pulsers 7a and 7b. In this state, the sequence controller 8 supplies one control pulse shown in FIG. 4A to the pulser 7a, and the pulser 7a generates a low voltage pulse shown in FIG. 4C accordingly. This low voltage pulse is supplied to the inner peripheral portion 2a of the piezoelectric elements 2, and a weak ultrasonic wave (low pressure ultrasonic wave) of about 10 bar is radiated in the body of the patient 4.

An echo reflected by the body upon radiation of the low pressure ultrasonic wave is received by the piezoelectric elements 2 and the echo received by the inner peripheral portion 2a is supplied to the receiver 12. In accordance with a time gate signal shown in FIG. 4D from the sequence controller 8, the receiver 12 extracts only a component of the echo from a portion close to the focal point of the piezoelectric elements 2. The receiver 12 amplifies and detects the extracted component, and holds its peak value, thereby generating an output signal shown in FIG. 4E. The output signal from the receiver 12 is supplied to the level detector 13 and compared with a predetermined threshold value Vth.

Since the calculus 5 has a higher acoustic impedance than those of the other soft tissues in the body of the patient 4 the intensity of the echo from the calculus 5 is high. For this reason, the output signal level from the receiver 12 becomes higher than the threshold value Vth, and the output from the level detector 13 becomes, e.g., a high level accordingly. To the contrary, if the calculus 5 falls outside the focal point of the piezoelectric elements 2 due to respiration, almost no echo is reflected from the body. Therefore, the output signal level from the receiver 12 becomes lower than the threshold value Vth, and the output from the level detector 13 becomes, e.g., a low level accordingly. The output from the level detector 13 is supplied to the sequence controller 8.

When the output from the level detector 13 becomes the high level, i.e., when the echo intensity exceeds the threshold value determined by Vth, the sequence controller 8 determines that the focal point and the portion of the calculus 5 coincide with each other and inverts the polarity of a switching control signal to the switch 9 for a predetermined time interval as shown in FIG. 4F. As a result, the switch 9 connects the high voltage power supply 10 to the pulsers 7a and 7b. At the same time, the sequence controller 8 supplies three control pulses shown in FIGS. 4A and 4B to the pulsers 7a and 7b, respectively. As a result, a high voltage pulse train shown in FIG. 4G is generated from the pulsers 7a and 7b and supplied to the inner and outer peripheral portions 2a and 2b of the piezoelectric elements 2, and an intense shock wave is generated and radiated on the calculus 5.

FIGS. 4A and 4B show three control pulses, but the number of control pulses may be determined arbitrarily, e.g., one, two, or more than three control pulses.

When the output from the level detector 13 is at low level, i.e., when the echo intensity does not reach the threshold value, the sequence controller 8 does not output the switching control signal to the switch 9. Therefore, no high voltage pulse is output. In this case, the pulser 7a is driven again to radiate the low pressure ultrasonic wave, thereby repeating the above operation.

In the above embodiment, the portion used to generate the low pressure ultrasonic wave for detecting a coincidence between the focal point of the piezoelectric elements 2 and the portion of the calculus 5 is the inner peripheral portion 2a, and the diameter of the inner peripheral portion 2a is substantially ½ the diameter of the portion (inner and outer peripheral portions 2a and 2b) used to generate the calculus destroying shock wave. Therefore, a focal point pressure distribution of the low pressure ultrasonic wave is widened in the radial direction to substantially twice that of the shock wave. Needless to say, however, the diameter of the inner peripheral portion need not be determined as above. For example, it may be approximately ⅔ of the portion used for generating the shock wave.

FIGS. 5A and 5B show this phenomenon, in which FIG. 5A shows the size of a spherical target (e.g., an alumina sphere having a diameter of 7 mm) as a model calculus to be irradiated with the low pressure ultrasonic wave, and FIG. 5B shows a measurement result of a distribution of echo intensity peak values in the radial direction obtained when the low pressure ultrasonic wave is radiated on the target. As shown in FIG. 5B, a half width in the echo intensity distribution is substantially identical to the diameter of the spherical target shown in FIG. 5A. Therefore, if the threshold value Vth in the level detector 13 is set to be a value corresponding to the echo intensity of the half width, the echo intensity exceeds the threshold value and the shock wave is generated even if the focal point coincides with an end portion of the calculus 5. As a result, the shock wave can be radiated on substantially the entire calculus to effectively perform calculus destruction.

In addition, in this embodiment, the switch 9 is provided before the pulsers 7a and 7b to selectively connect the high and low voltage power supplies 10 and 11 to them, thereby selectively generating the boosted high and low voltage pulses from the pulsers 7a and 7b. Therefore, since the switch 9 need only handle low voltage and current, a compact switch can be used. In addition, only one switch is required although the number of pulsers (piezoelectric elements) is increased, resulting in a simple arrangement.

FIG. 6 shows an apparatus according to the second embodiment of the present invention.

Referring to FIG. 6, piezoelectric elements 30 are constituted by concentrically arranging five ring-like piezoelectric elements 31 to 35, and pulsers 41 to 45 each having the same arrangement as that shown in FIG. 3 are connected to the piezoelectric elements 31 to 35, respectively. In this case, in order to generate a shock wave for calculus destruction, the pulsers 41 to 45 are connected to a high voltage power supply 10 via a switch 9, and control pulses are simultaneously supplied from a sequence controller 8 to the pulsers 41 to 45.

In order to generate a low pressure ultrasonic wave for detecting a coincidence between a portion of a calculus 5 and a focal point of the piezoelectric elements 30, the pulsers 41 to 45 are connected to a low voltage power supply 11 via the switch 9, and control pulses are supplied from the sequence controller 8 to the pulsers 41 to 45 with relative time differences therebetween. Therefore, low voltage pulses are applied to the piezoelectric elements 31 to 35 with time differences therebetween.

In this case, the time differences upon application of the low voltage pulses to the piezoelectric elements 31 to 35 are set such that a focused state of an ultrasonic wave is widened at its focal point. The fact that a focused state of a radiated ultrasonic wave can be changed by giving a time difference to a drive timing of each piezoelectric element of a piezoelectric element arrangement is known from, e.g., a conventional ultrasonic diagnostic apparatus. By giving predetermined time differences to control pulses from the sequence controller 8 to the pulsers 41 to 45 by utilizing the above technique, the focal point pressure distribution of the low pressure ultrasonic wave can be made wider than that of the shock wave.

Echoes received by the piezoelectric elements 31 to 35 are preferably delayed by a delay circuit 50 by the same time differences given to the low pressure ultrasonic waves radiated from the elements 31 to 35. Thereafter, as in the above embodiment, the delayed echoes are supplied to a receiver 12 and compared with a threshold value Vth by a level detector 13, thereby determining whether the echo intensity exceeds the threshold value. If the echo intensity exceeds the threshold value, the sequence controller 8 simultaneously supplies control pulses to the pulsers 41 to 45, and the high voltage power supply 10 is connected to the pulsers 41 to 45 via the switch 9. As a result, high voltage pulses are output from the pulsers 41 to 45, and the shock waves are generated from the piezoelectric elements 31 to 35 accordingly.

Figure 7:
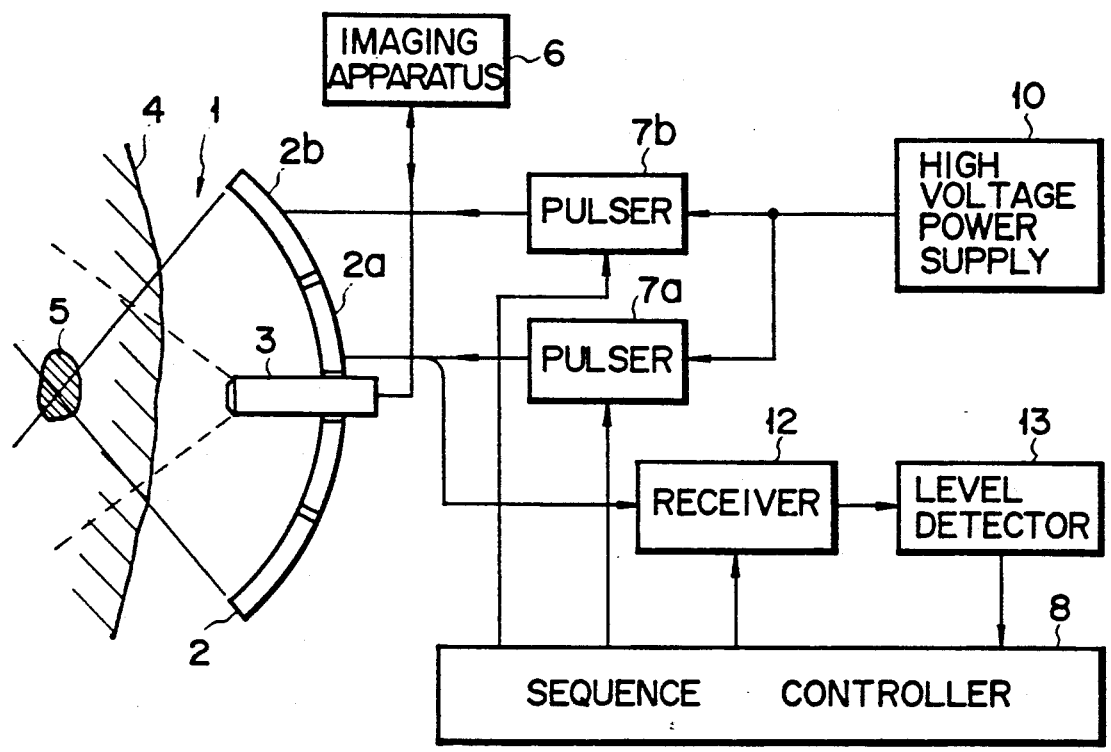
FIG. 7 is a block diagram showing an arrangement of a calculus destroying apparatus according to the third embodiment of the present invention.

FIG. 7 shows an apparatus according to still another embodiment of the present invention.

Figure 8:
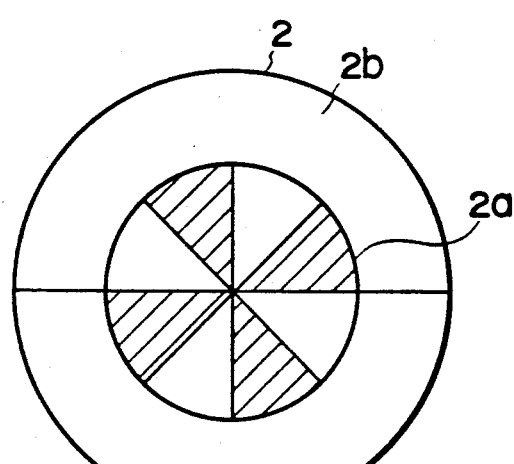
FIG. 8 is a front view schematically showing an arrangement of piezoelectric elements of the apparatus shown in FIG. 7.

In this apparatus, the switch 9 and the low voltage power supply 11 shown in FIG. 2 are not used, and a high voltage power supply 10 is directly connected to pulsers 7a and 7b. As in the embodiment shown in FIG. 2, piezoelectric elements 2 are divided into inner and outer peripheral portions 2a and 2b which can be driven independently of each other and are connected to the pulsers 7a and 7b. As shown in FIG. 8, however, the inner peripheral portion 2a is divided into a plurality of (in FIG. 8, eight) portions in the circumferential direction. The pulser 7a is connected to only hatched portions of the inner peripheral portion 2a shown in FIG. 8, while the pulser 7b is connected to the entire inner peripheral portion 2a and the outer peripheral portion 2b. In addition, a receiver 12 is connected to only the hatched portions of the inner peripheral portion 2a.

In this apparatus, a pulse voltage generated from the pulser 7a is applied to only the hatched portions of the inner peripheral portion 2a of the piezoelectric elements 2. Therefore, even if the pulse voltage is high, a generated ultrasonic wave has a low pressure. In addition, the maximum diameter of the hatched portions is smaller than the maximum diameter of the partial inner and outer peripheral portions 2a and 2b used to generate a calculus destroying shock wave. Therefore, a low pressure ultrasonic wave for detecting a coincidence between a focal point and a portion of a calculus 5 can be generated by only preparing the high voltage power supply 10 as a power supply. In addition, since a focal point pressure distribution of the low pressure ultrasonic wave becomes larger than that of the shock wave, desired objects can be achieved.

The present invention is not limited to the above embodiments but can be variously modified and carried out without departing from the spirit and scope of the invention. For example, the piezoelectric elements 2 are divided into the inner and outer peripheral portions 2a and 2b in FIG. 2. The piezoelectric elements, however, may be divided into a larger number of portions and low voltage pulses may be applied to several piezoelectric elements at the inner peripheral side simultaneously or with time differences, thereby radiating a low pressure ultrasonic wave for detecting a coincidence between a focal point of the piezoelectric elements and a calculus portion.

What is claimed is:

1. A calculus destroying apparatus comprising:
    a vibration generating source having a plurality of piezoelectric elements;
    first driving means for driving said piezoelectric elements so that a shock wave for calculus destruction having a predetermined focal point pressure distribution is generated from said piezoelectric elements;
    second driving means for driving at least some of said piezoelectric elements so that a low pressure ultrasonic wave having a lower pressure and a wider focal point pressure distribution than those of the shock wave is generated from said piezoelectric elements;
    receiving means for receiving an echo of the low pressure ultrasonic wave from inside a patient's body via said piezoelectric elements; and control means for activating said second driving means prior to activation of said first driving means, and activating said first driving means when an intensity of the echo received by said receiving means exceeds a predetermined threshold value.

2. An apparatus according to claim 1, wherein said first driving means includes means for driving said piezoelectric elements by a pulse having a comparatively high voltage.

3. An apparatus according to claim 1, wherein said second driving means includes means for driving at least some of said piezoelectric elements by a pulse having a comparatively low voltage.

4. An apparatus according to claim 1, wherein said piezoelectric elements include a plurality of concentrically arranged piezoelectric elements.

5. An apparatus according to claim 4, wherein said second driving means includes means for driving only those piezoelectric elements on an inner peripheral side of said piezoelectric elements so as to generate the low pressure ultrasonic wave having a lower pressure and a wider focal point pressure distribution than those of the shock wave.

6. An apparatus according to claim 4, wherein said second driving means includes means for driving each of said piezoelectric elements with a predetermined time difference so as to generate the low pressure ultrasonic wave having a lower pressure and a wider focal pressure distribution point than those of the shock wave.

7. A calculus destroying apparatus comprising:
    a vibration generating source having a plurality of piezoelectric elements;
    driving means having a first driving mode for driving said piezoelectric elements so that a shock wave for calculus destruction is generated from said piezoelectric elements, and a second driving mode for driving at least some of said piezoelectric elements so that a low pressure ultrasonic wave having a lower pressure and a wider focal point pressure distribution than those of the shock wave is generated from said piezoelectric elements;
    receiving means for receiving an echo of the low pressure ultrasonic wave from inside a patient's body via said piezoelectric elements; and
    control means for operating said driving means in the second driving mode prior to an operation in the first driving mode, and operating said driving means in the first driving mode when an intensity of the echo received by said receiving means exceeds a predetermined threshold value.

8. An apparatus according to claim 7, wherein said driving means includes means for driving said piezoelectric elements by a pulse having a comparative high voltage in the first driving mode, and driving at least some of said piezoelectric elements by a pulse having a comparatively low voltage in the second driving mode.

9. An apparatus according to claim 7, wherein said driving means includes means for driving at least those piezoelectric elements on an inner peripheral side of said piezoelectric elements, in the second driving mode, so as to generate the low pressure ultrasonic wave having a lower pressure and a wider focal point pressure distribution than those of the shock wave.

10. An apparatus according to claim 7, wherein said driving means includes means for driving each of said piezoelectric elements with a predetermined time difference in the second driving mode so as to generate the low pressure ultrasonic wave having a lower pressure and a wider focal point pressure distribution than those of the shock wave.

11. A calculus destroying apparatus comprising:
imaging ultrasonic transmitting/receiving means for transmitting/receiving an imaging ultrasonic wave;
image processing means for obtaining an ultrasonic image in accordance with an ultrasonic echo obtained by said imaging ultrasonic transmitting/receiving means;
a vibration generating source having said imaging ultrasonic transmitting/receiving means therein, constituted by a plurality of piezoelectric elements;
first driving means for driving said piezoelectric elements so that a shock wave for calculus destruction having a predetermined focal point pressure distribution is generated from said piezoelectric elements;
second driving means for driving at least some of said piezoelectric elements so that a low pressure ultrasonic wave having a lower pressure and a wider focal point pressure distribution than those of the shock wave is generated from said piezoelectric elements;
receiving means for receiving an echo of the low pressure ultrasonic wave from inside a patient's body via said piezoelectric elements; and
control means for activating said second driving means prior to activation of said first driving means, and activating said first driving means when an intensity of the echo received by said receiving means exceeds a predetermined threshold value.

12. An apparatus according to claim 11, wherein said first driving means includes means for driving said piezoelectric elements by a pulse having a comparatively high voltage.

13. An apparatus according to claim 11, wherein said second driving means includes means for driving at least some of said piezoelectric elements by a pulse having a comparatively low voltage.

14. An apparatus according to claim 11, wherein said piezoelectric elements include a plurality of concentrically arranged piezoelectric elements.

15. An apparatus according to claim 14, wherein said second driving means includes means for driving only those piezoelectric elements on an inner peripheral side of said piezoelectric elements so as to generate the low pressure ultrasonic wave having a lower pressure and a wider focal point pressure distribution than those of the shock wave.

16. An apparatus according to claim 14, wherein said second driving means includes means for driving each of said piezoelectric elements with a predetermined time difference so as to generate the low pressure ultrasonic wave having a lower pressure and a wider focal pressure distribution point than those of the shock wave.

* * * * *